United States Patent
Tsuchiya

(10) Patent No.: US 8,611,500 B2
(45) Date of Patent: Dec. 17, 2013

(54) X-RAY IMAGING APPARATUS AND MEASUREMENT METHOD

(75) Inventor: Keiji Tsuchiya, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 343 days.

(21) Appl. No.: 13/177,684

(22) Filed: Jul. 7, 2011

(65) Prior Publication Data

US 2012/0027180 A1 Feb. 2, 2012

(30) Foreign Application Priority Data

Jul. 30, 2010 (JP) ................................. 2010-172728

(51) Int. Cl.
*H05G 1/56* (2006.01)

(52) U.S. Cl.
USPC ............................................. 378/114; 378/62

(58) Field of Classification Search
USPC .............. 378/62, 98.8, 114–116; 250/370.08, 250/370.09, 370.11
See application file for complete search history.

(56) References Cited

U.S. PATENT DOCUMENTS

| | | | |
|---|---|---|---|
| 5,818,898 A | 10/1998 | Tsukamoto et al. | 378/98.8 |
| 6,977,988 B2 | 12/2005 | Niwa | 378/95 |
| 7,945,015 B2 | 5/2011 | Tsujii et al. | 378/26 |
| 2002/0050568 A1 | 5/2002 | Nonaka | 250/370.09 |
| 2003/0086523 A1 | 5/2003 | Tashiro et al. | 378/19 |
| 2004/0240612 A1 | 12/2004 | Suzuki | 378/91 |

FOREIGN PATENT DOCUMENTS

| | | |
|---|---|---|
| EP | 1035421 | 9/2000 |
| JP | 62-276798 | 12/1987 |
| JP | 2002-301053 | 10/2002 |
| JP | 2004-166728 | 6/2004 |

OTHER PUBLICATIONS

Extended European Search Report, dated Nov. 30, 2011, issued in counterpart European Patent Application No. 11172785.5 (in English).

*Primary Examiner* — Courtney Thomas
(74) *Attorney, Agent, or Firm* — Fitzpatrick, Cella, Harper & Scinto

(57) ABSTRACT

An X-ray imaging apparatus which obtains an X-ray image, the apparatus includes: an imaging unit including a plurality of detecting elements adapted to convert X-rays generated by an X-ray generating apparatus which outputs or stops X-rays in accordance with an operation instruction into an image signal; and an obtaining unit adapted to obtain an operation start timing of the X-ray generating apparatus based on an image signal output from the imaging unit and obtain a difference between a timing of an operation instruction to the X-ray generating apparatus and the operation start timing.

10 Claims, 8 Drawing Sheets

X-RAY IMAGING APPARATUS AND MEASUREMENT METHOD

BACKGROUND OF THE INVENTION

1. Field of the Invention

The present invention relates to an X-ray imaging apparatus and a measurement method and, more particularly, to a technique for measuring delays associated with X-ray output operation.

2. Description of the Related Art

An X-ray imaging apparatus is known, which uses a flat panel detector including a two-dimensional array of detecting elements and TFTs formed from an amorphous silicon and polysilicon, as materials that are deposited and formed on a glass substrate. Such apparatuses vary in type, but are generally configured such that when X-rays strike the flat panel detector, the phosphor wavelength-converts X-rays into visible light. The detecting elements convert the converted light into charges and store the charges. When the TFTs are turned on for each row, the charges stored in the flat panel detector are sequentially read and converted into pixel values. Using such a flat panel detector, an X-ray imaging apparatus generates an image according to the intensity distribution of X-rays, on the flat panel detector, which are transmitted through an object placed between an X-ray generating apparatus (X-ray source) which emits X-rays and the flag panel detector.

Recently, flat panel detectors capable of capturing moving images as well as still images have been developed.

The following can influence the quality of moving images when capturing a moving image performed by repeatedly capturing still images at a high speed:

the difference between the timing at which the X-ray generating apparatus receives a signal indicating X-ray exposure and the timing at which the X-ray generating apparatus starts X-ray exposure in accordance with the signal (X-ray exposure start delay time), and the difference between the timing at which the X-ray generating apparatus receives a signal indicating when X-ray exposure has stopped and the timing at which the X-ray generating apparatus stops X-ray exposure in accordance with the signal (X-ray exposure stop delay time).

This point will be described with reference to FIGS. 7 to 9. FIG. 7 is a timing chart showing the relationship between an X-ray exposure signal, X-ray intensity, and read in the moving image capturing mode.

The flat panel detector alternately repeats storing and reading charges originating from X-ray exposure. Referring to FIG. 7, "read" indicates periods during which charges are read from the flat panel detector, "Hi" indicates a period during which charges are read, and "Lo" indicates a period during which no charge is read (charges are stored in the case shown in FIG. 7).

When capturing an image by reading charges, offset correction is generally performed. A technique is known where offset correction is performed for a moving image capturing apparatus including a flat panel detector and driving the apparatus (Japanese Patent Laid-Open No. 2002-301053). FIG. 7 shows a timing chart when an X-ray image is generated by reading charges twice per X-ray exposure, and subtracting an image read without X-ray exposure from an image read after X-ray exposure.

Referring to FIG. 7, "X-ray exposure signal" indicates the transition of an X-ray exposure signal supplied to the X-ray generating apparatus, with a Hi period of the X-ray exposure signal indicating X-ray exposure, and a Lo period of the signal indicating the stop of X-ray exposure. The X-ray generating apparatus (not shown) starts X-ray exposure when the X-ray exposure signal goes Hi, and stops X-ray exposure when the X-ray exposure signal goes Lo. It takes a certain time from the instant the X-ray exposure signal goes Hi to the instant X-ray exposure actually starts (X-ray exposure start delay time). It also takes a certain time from the instant the X-ray exposure signal goes Lo to the instant X-ray exposure actually stops (X-ray exposure stop delay time). Referring to FIG. 7, "X-ray intensity" indicates the transition of the intensity of X-rays actually output from the X-ray generating apparatus. Referring to FIG. 7, reference symbol Ta denotes an X-ray exposure start delay time; and Tb, an X-ray exposure stop delay time. In addition, X-ray exposure is performed during storage of charges.

If the frame rate in moving image capturing is high, the magnitudes of the X-ray exposure start delay time and X-ray exposure stop delay time become large relative to the frame interval. FIG. 8 is a timing chart showing an X-ray exposure signal, X-ray intensity, and read when the frame rate in the moving image capturing mode is high.

As the frame rate in moving image capturing increases, since the charge read time is constant, the charge storage period decreases. Actual X-ray exposure may overlap reading of charges because the X-ray exposure is accompanied by an X-ray exposure start delay time and an X-ray exposure stop delay time. Referring to FIG. 8, the hatched portion indicates a portion where actual X-ray exposure overlaps a charge read. Reference symbol Tc denotes an overlap time.

It is generally necessary to emit a predetermined dose of X-rays to capture an X-ray image. If, therefore, X-ray exposure overlaps a charge read, since the intensity of emitted X-rays is not reflected in the stored charges, the quality of an X-ray image deteriorates.

To emit the predetermined dose of X-rays, it is conceivable to secure a predetermined period of time during which an X-ray exposure signal is set Hi or shorten a "Hi" period of the X-ray exposure signal and increase an X-ray tube current or X-ray tube voltage for the X-ray generating apparatus. As in the latter case, an increase in X-ray tube current in the X-ray generating apparatus will lead to an increase in cost, whereas an excessive increase in X-ray tube voltage will lead to a decrease in the contrast of a captured X-ray image. For this reason, to emit the predetermined dose of X-rays, the technique of securing a predetermined period of time during which the X-ray exposure signal is set Hi is generally used. In this case, in order to increase the frame rate in moving image capturing, it is necessary to minimize the time interval from the end of charge reading to the start of X-ray exposure and the time interval from the end of X-ray exposure and the start of charge reading.

FIG. 9 is a timing chart showing the relationship between an X-ray exposure signal, X-ray intensity, and read when X-ray exposure starts concurrently with the end of charge reading, and charge reading starts concurrently with the end of X-ray exposure.

Referring to FIG. 9, the X-ray exposure start delay time Ta and an X-ray exposure stop delay time Tb are measured in advance. The X-ray exposure signal is set Hi the measured time Ta earlier than the timing of the end of charge reading. In addition, the X-ray exposure signal is set Lo the measured time Tb earlier than the timing of the start of charge reading. Performing this control can maximize the frame rate without making an actual X-ray exposure period overlap a charge read period.

In general, a flat panel detector can be connected to various types of X-ray generators depending on the region to be imaged or the imaging purpose. However, different X-ray generators differ in X-ray exposure start delay time and X-ray exposure stop delay time. For this reason, it is necessary to measure an X-ray exposure start delay time and an X-ray exposure stop delay time in advance for each apparatus to be used.

Japanese Patent Laid-Open No. 62-276798 discloses an arrangement for measuring an X-ray exposure start delay time and an X-ray exposure stop delay time, and correcting the X-ray exposure start timing and the X-ray exposure stop timing by correcting the measured delay times. In addition, Japanese Patent Laid-Open No. 2004-166728 discloses an arrangement in which an X-ray detector different from a flat panel detector is provided outside the flat panel detector to measure a read timing.

With regard to the arrangement disclosed in Japanese Patent Laid-Open No. 62-276798, there is no description about a specific technique of measuring the X-ray exposure start delay time Ta and the X-ray exposure stop delay time Tb. It is generally necessary to additionally prepare an X-ray detector for measuring an actual X-ray intensity and to measure an output from the X-ray detector and an X-ray exposure signal and a read signal with an oscilloscope or the like. This measurement requires much time and labor.

In addition, the arrangement disclosed in Japanese Patent Laid-Open No. 2004-166728 requires an additional X-ray detector outside the flat panel detector to measure the X-ray exposure start delay time Ta and the X-ray exposure stop delay time Tb, and hence has the problem of high cost.

SUMMARY OF THE INVENTION

The present invention has been made in consideration of the above problems, and aims to provide a technique of easily measuring delay times occurring at the start and stop of X-ray exposure at a low cost without providing any special arrangement.

According to one aspect of the present invention, an X-ray imaging apparatus which obtains an X-ray image, the apparatus includes: an imaging unit including a plurality of detecting elements adapted to convert X-rays generated by an X-ray generating apparatus which outputs or stops X-rays in accordance with an operation instruction into an image signal; and an obtaining unit adapted to obtain an operation start timing of the X-ray generating apparatus based on an image signal output from the imaging unit and obtain a difference between a timing of an operation instruction to the X-ray generating apparatus and the operation start timing.

According to another aspect of the present invention, a method of measuring a delay time of X-ray exposure by an X-ray imaging apparatus which obtains an X-ray image, the method includes the steps of: causing an X-ray generating apparatus to change an X-ray output state in accordance with an operation signal; sequentially reading image signals from an imaging unit adapted to convert the X-rays into image signals; and measuring a delay of operation of the generating apparatus relative to the operation signal by analyzing the image signal.

Further features of the present invention will become apparent from the following description of exemplary embodiments (with reference to the attached drawings).

DESCRIPTION OF THE EMBODIMENTS

The embodiments of the present invention will be described in detail below with reference to the accompanying drawings.

(Arrangement of X-Ray Imaging Apparatus)

Figure 1:
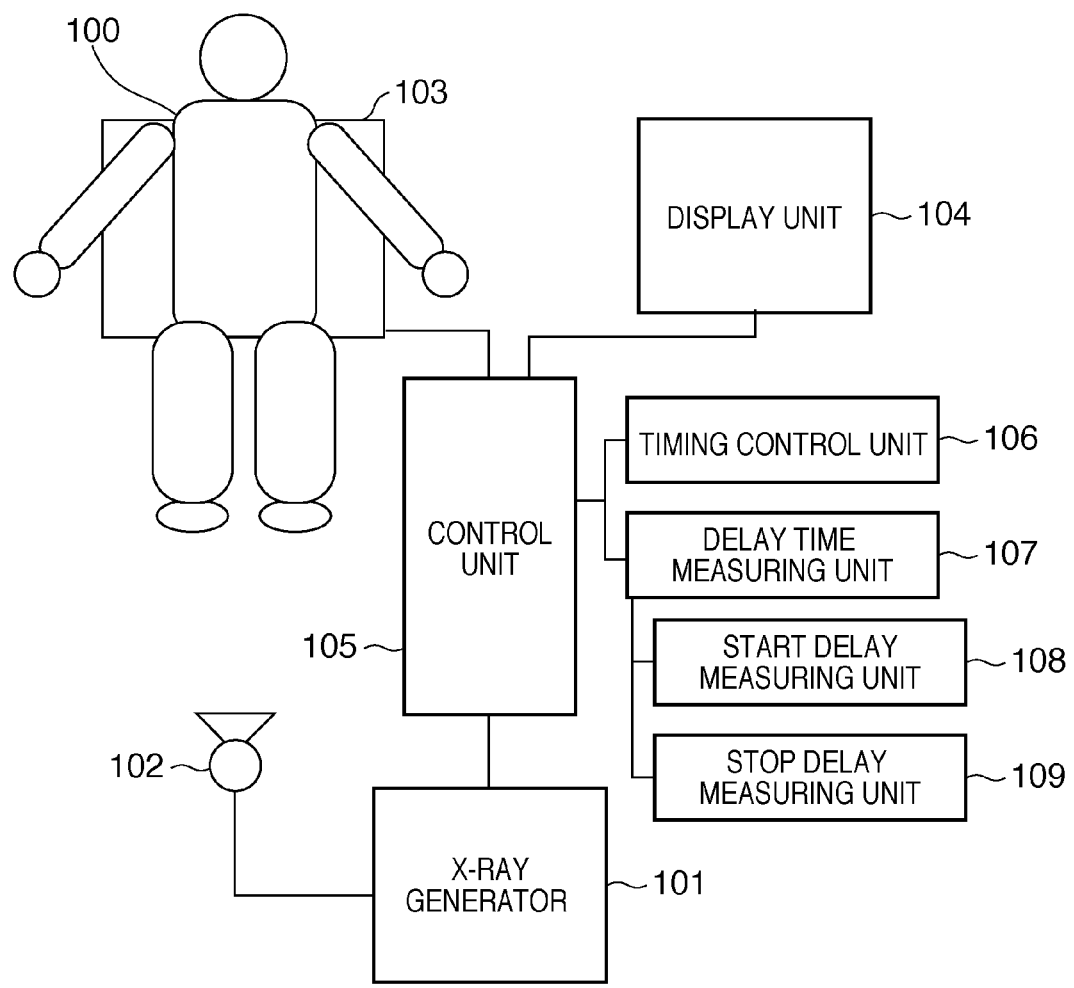
FIG. 1 is a schematic block diagram showing the arrangement of an X-ray imaging apparatus according to an embodiment of the present invention.

FIG. 1 is a schematic block diagram of an X-ray imaging apparatus according to this embodiment. Reference numeral 101 denotes an X-ray generator which controls X-ray exposure; 102, an X-ray tube 102 which emits X-rays; 100, an object to be examined (object to be imaged); 103, a flat panel detector for detecting X-rays transmitted through the object 100; 104, a display unit for displaying an X-ray image read from the flat panel detector 103; and 105, a control unit which controls the overall X-ray imaging apparatus.

The control unit 105 is connected to the X-ray generator 101 via an X-ray exposure signal. When the control unit 105 controls an X-ray exposure signal (to Hi or Lo), the X-ray generator 101 starts or stops X-ray exposure. The control unit 105 performs control to execute X-ray exposure once in the still image capturing mode and continuously emit X-rays in a pulse manner in the moving image capturing mode. Note that when measuring delay times in X-ray exposure, imaging is performed in the absence of an object to be examined as an object to be imaged.

The control unit 105 is connected to the flat panel detector 103 via a read start signal, and controls the read start signal (to Hi or Lo) to make the flat panel detector 103 start reading. The control unit 105 is also connected to the flat panel detector 103 via a MODE signal line, and controls the MODE signal line (to Hi or Lo) to switch between the still image capturing mode and the moving image capturing mode. In this embodiment, turning on the gate lines of the flat panel detector 103 for each row will sequentially read charges from the flat panel detector 103. In this manner, the embodiment obtains an image by reading charges from detecting element constituting the flat panel detector for each row. The scanning speed associated with charge reading is constant, and is known in advance.

In addition, the control unit 105 includes a timing control unit 106 which controls the X-ray exposure timing and the read timing of the flat panel detector 103. The timing control unit 106 generally performs control to perform X-ray exposure during a storage period of the flat panel detector 103. When measuring an X-ray exposure start delay time Ta and an X-ray exposure stop delay time Tb, in particular, the timing control unit 106 controls the X-ray generator 101 to start and stop X-ray exposure during the read operation of the flat panel detector 103.

The control unit 105 also includes a delay time measuring unit (X-ray exposure delay time measuring unit) 107 which measures a delay time associated with X-ray exposure by analyzing an image obtained by X-ray exposure during read operation of the flat panel detector 103. The delay time measuring unit 107 includes a start delay measuring unit (X-ray exposure start delay time measuring unit) 108 and a stop delay measuring unit (X-ray exposure stop delay time measuring time unit) 109. The start delay measuring unit 108 measures the X-ray exposure start delay time from the instant a signal indicating X-ray exposure is input to the instant X-rays are actually emitted. The stop delay measuring unit 109 measures the X-ray exposure stop delay time from the instant a signal indicating the stop of X-ray exposure is input to the instant X-ray exposure actually stops. As will be described later, this embodiment measures the delay time of X-ray exposure based on the position of the boundary between a region where there is a change in pixel value in an image obtaining by emitting uniform X-rays and performing scanning at a constant speed and a region where there is no change in pixel value in the image, and a scanning speed associated with charge reading.

(Arrangement of Flat Panel Detector)

Figure 2:
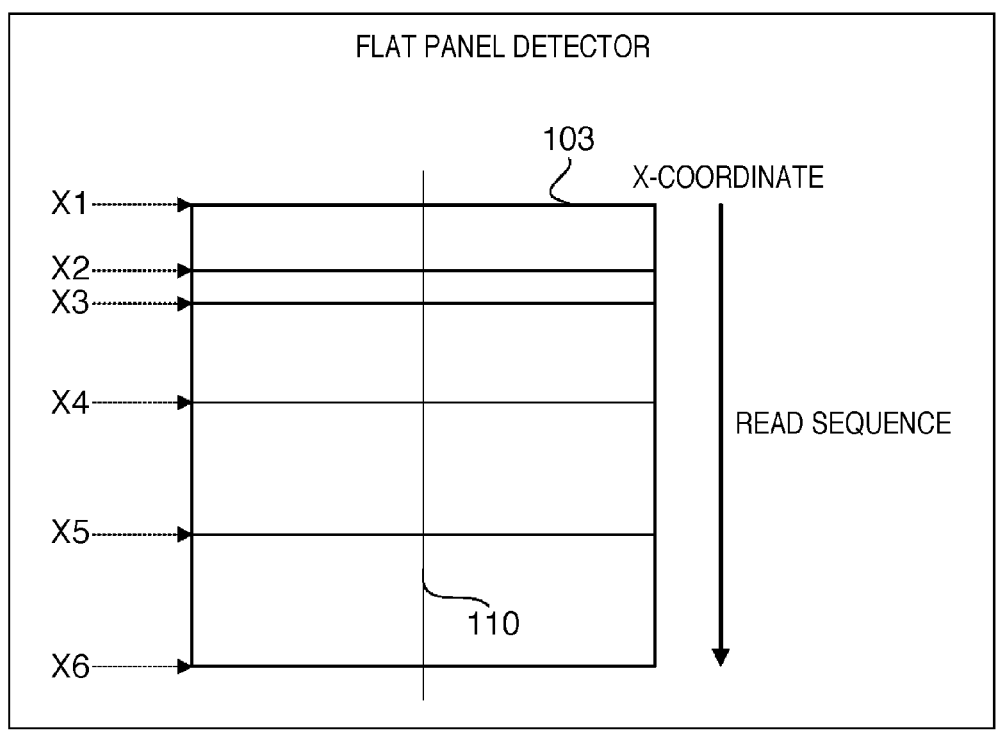
FIG. 2 is a schematic plan view showing the arrangement of a flat panel detector according to the embodiment of the present invention.

FIG. 2 is a schematic plan view of the flat panel detector 103. The flat panel detector 103 in FIG. 2 has an arrangement in which detecting elements for converting received X-ray signals into charges are provided in a matrix form. In practice, the number of detecting elements is about 2000×2000. The charges converted from X-ray signals by the detecting elements are respectively stored in the corresponding capacitors.

Referring to FIG. 2, the X-axis is set in the longitudinal direction on the drawing surface. Assume that in this embodiment, the read sequence of the detecting elements coincides with the direction in which X-coordinates increase (in the downward direction in this embodiment). In addition, X1 represents a coordinate of the uppermost row of the flat panel detector 103, and X6 represents a coordinate of the lowermost row. Coordinates X2 to X5 are coordinates between the coordinates X1 and X6. The embodiment reads charges from the detecting elements constituting the flat panel detector row by row at a constant speed. The coordinates X2 and X4 respectively correspond to the positions of a leading edge and trailing edge of an X-ray exposure signal, and the coordinates X3 and X5 respectively correspond to the positions of the start and end time points of actual X-ray exposure. In the embodiment, since times T1, T2, T4, and T6 are determined in advance, it is possible to calculate the values of X1, X2, X4, and X6 and set them in the apparatus in advance. Note however that it is possible to calculate the values of X1, X2, X4, and X6 for each measurement of an X-ray exposure delay in accordance with the timing of switching of an X-ray exposure signal.

A vertical line 110 indicates a position in the flat panel detector 103 at which pixel values are detected. The position of the vertical line 110 in FIG. 2 is an example for facilitating the understanding of the description, and is not limited to the example.

(X-Ray Exposure in Moving Image Capturing Mode)

Figure 3:
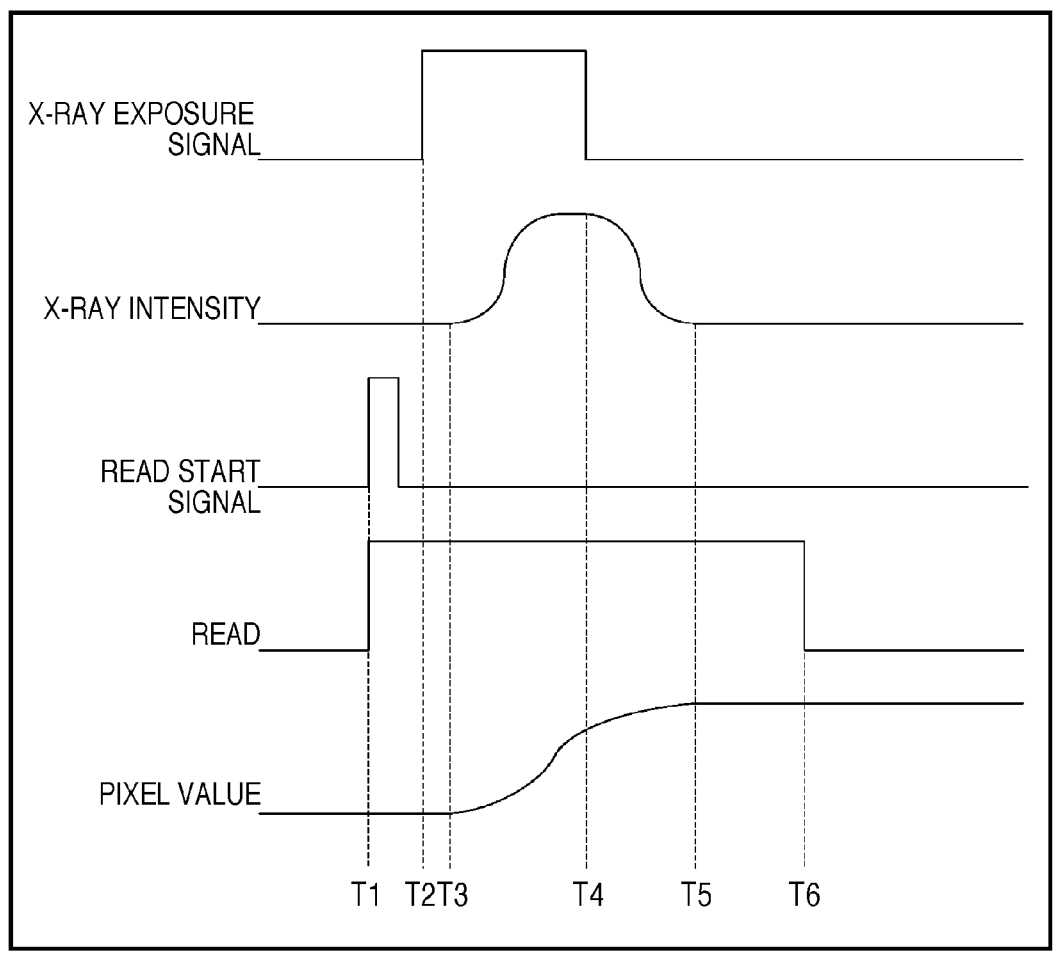
FIGS. 3, 4, 5, and 6 are timing charts for measurement of X-ray exposure delay times according to the embodiment of the present invention.

FIG. 3 is a timing chart showing an X-ray exposure signal, X-ray intensity, read start signal, charge read, and temporal transition of read pixel value when X-ray exposure is performed once in the moving image capturing mode. Times T1 to T6 correspond to the times when the X-coordinates X1 to X6 of the flat panel detector 103 shown in FIG. 2 are read.

Referring to FIG. 3, the timing control unit 106 sets a read start signal Hi at time T1, and sets an X-ray exposure signal Hi during charge reading. When the input read start signal is set Hi, the flat panel detector 103 starts reading charges. When the input X-ray exposure signal is set Hi, the X-ray generator 101 controls the X-ray tube 102 to emit X-rays. In addition, the timing control unit 106 sets the read start signal Lo after the lapse of a predetermined time (between times T1 and T2 in the case shown in FIG. 3), and sets the X-ray exposure signal Lo during charge reading (time t4 in the case shown in FIG. 3). The flat panel detector 103 continues read operation until reading all the rows without being influenced by the read start signal even if it goes Lo. On the other hand, when the input X-ray exposure signal goes Lo, the X-ray generator 101 stops X-ray exposure. In this manner, the timing control unit 106 performs control to perform X-ray exposure during charge reading. The period during which the timing control unit 106 sets an X-ray exposure signal Hi varies depending on the X-ray imaging apparatus to be used. When using an X-ray imaging apparatus configured to perform moving image capturing at a frame rate of 30 FPS, this period is generally about several ms.

Figure 7:
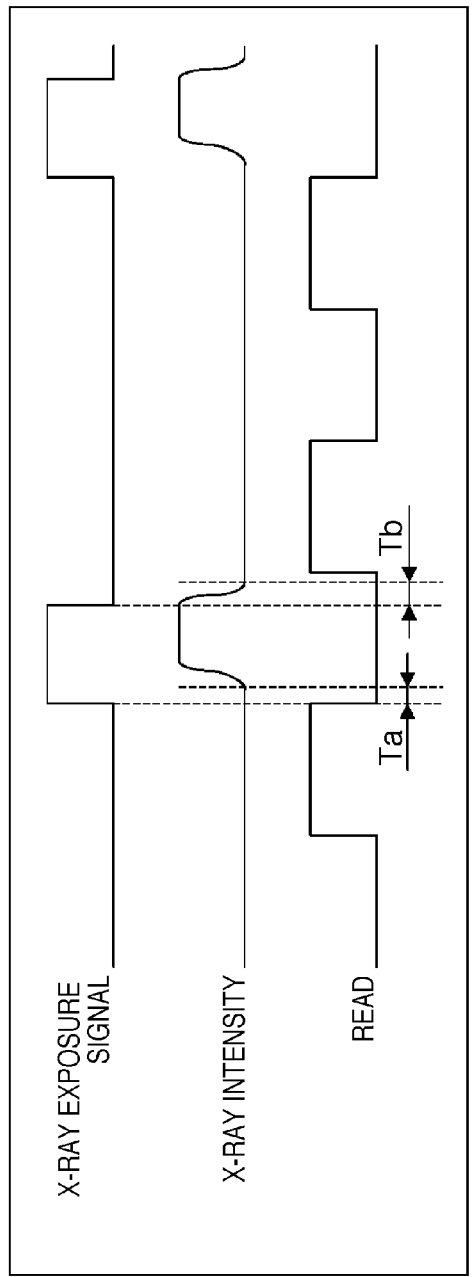
FIGS. 7, 8, and 9 are timing charts associated with X-ray exposure and charge reading in moving image capturing.
Figure 8:
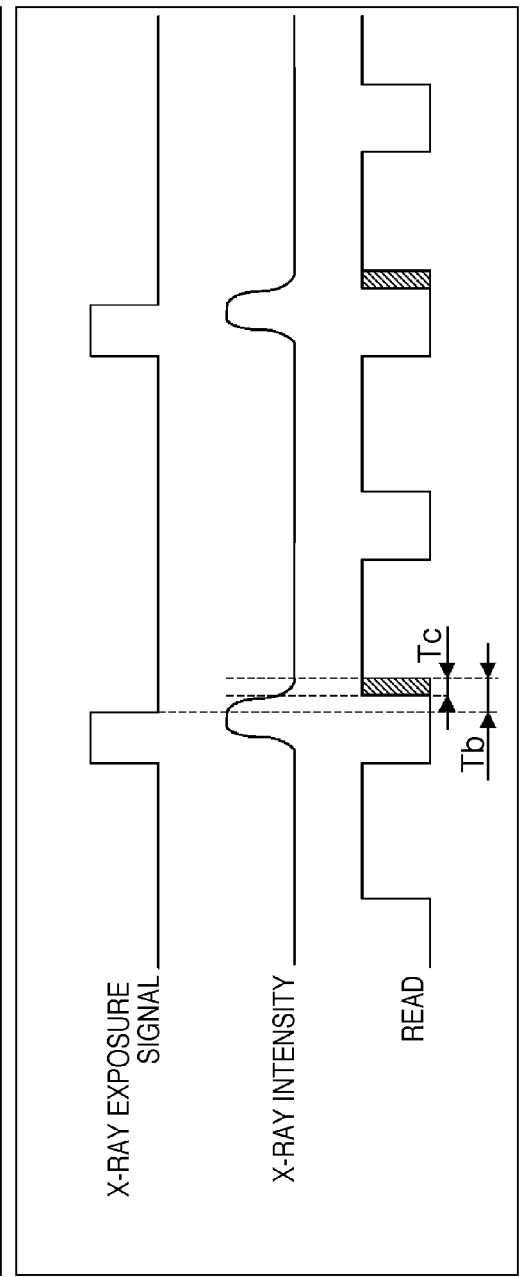
Figure 9:
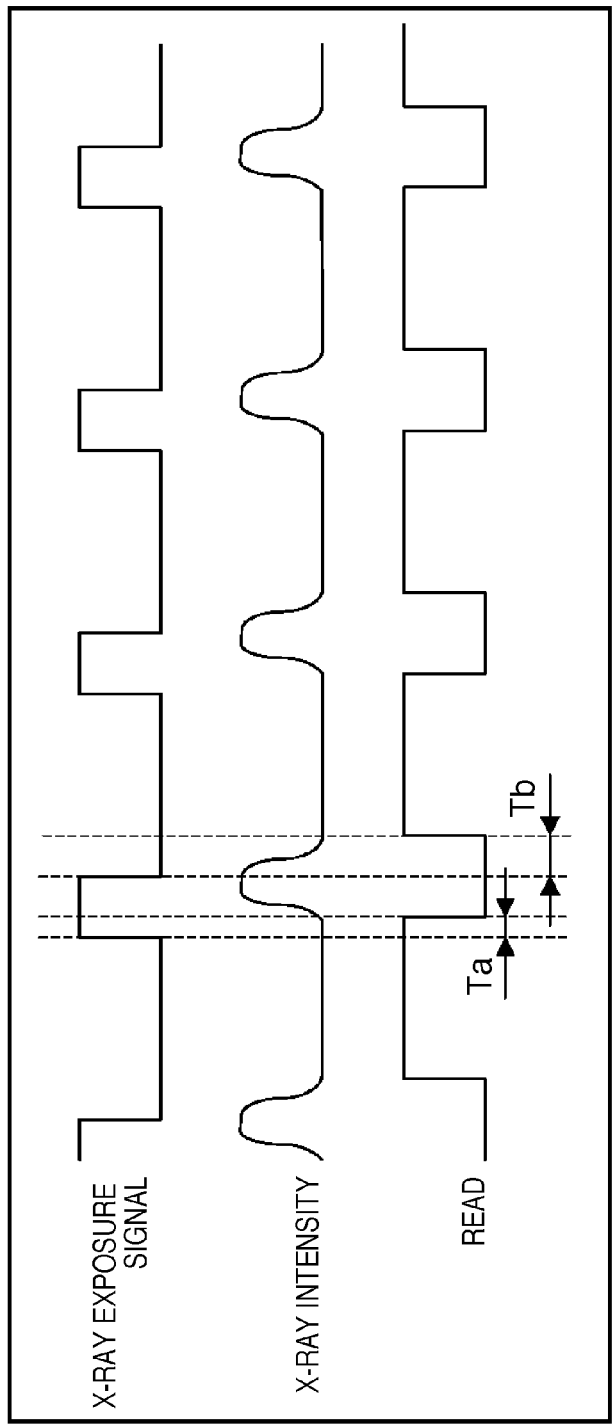

Referring to FIG. 3, like FIG. 7, "X-ray exposure signal" indicates a signal for performing X-ray exposure; "X-ray intensity", the intensity of X-rays actually emitted; "read", reading of charges from the flat panel detector; and "pixel value", pixel values on the vertical line 110 of the flat panel detector in FIG. 2.

As described above, times T1 to T6 correspond to the times when the X-coordinates X1 to X6 of the flat panel detector 103 shown in FIG. 2 are read. That is, time T1 is the time when charge reading starts, and is also the time when charge is read from the coordinate X1 of the flat panel detector 103. Time T6 is the time when charge reading stops, and is also the time when charge is read from the coordinate X6 of the flat panel detector 103. Time T2 is the time when the X-ray exposure signal is set Hi, and is also the time when charge is read from the coordinate X2 of the flat panel detector 103. When the X-ray exposure signal goes Hi, the X-ray generator 101 emits X-rays from the X-ray tube 102. As has been described, however, X-ray exposure actually starts from time T3 due to an X-ray exposure start delay time. Time T3 is also the time when charge is read from the coordinate X3 of the flat panel detector 103. Time T4 is the time when the X-ray exposure signal is set Lo, and is also the time when charge is read from the coordinate X4 of the flat panel detector 103. When the X-ray exposure signal goes Lo, the X-ray generator 101 stops X-ray exposure from the X-ray tube 102. However, due to an X-ray exposure stop delay time, X-ray exposure actually stops at time T5. Time T5 is the time when charge is read from the coordinate X5 of the flat panel detector 103. Note, as described above, that the values of X1, X2, X4, and X6 are known in advance, and are set in the apparatus.

(Measurement of Delay Times Associated with X-Ray Exposure)

A procedure for measuring delay times associated with X-ray exposure by the start delay measuring unit 108 and the stop delay measuring unit 109 will be described next. The start delay measuring unit 108 and the stop delay measuring unit 109 measure an X-ray exposure start delay time and an X-ray exposure stop delay time by analyzing an image obtained by X-ray exposure during charge reading.

More specifically, as shown in FIG. 3, the pixel value remains constant from time T1 when charge reading starts to time T3 when X-rays are actually emitted. After time T3, the pixel value increases until time T5 when X-ray exposure actually stops. At this time, the pixel value becomes the value obtained by integrating X-ray intensities from time T3 when X-rays are actually emitted to time T5 when charge reading starts. Subsequently, when X-ray exposure actually stops, the pixel value remains constant until time T6 when pixel value reading ends.

As described above, charges are read from the flat panel detector 103 row by row in a predetermined time (Tf in this embodiment). The value of Tf is known in advance, and is set in the apparatus. Letting T2 be the time when an X-ray exposure signal is set Hi, and T4 be the time when the X-ray exposure signal is set Lo, the coordinates X2 and X4 read at times T2 and T4 can be calculated by $$X2=X1+(T2-T1)/Tf \quad (1)$$

$$X4=X1+(T4-T1)/Tf \quad (2)$$

The start delay measuring unit 108 therefore calculates the X-ray exposure start delay time Ta according to the following equation using the coordinate X2 calculated by equation (1) and the coordinate X3 corresponding to the time when the pixel value increases:

$$Ta=(X3-X2)/Tf \quad (3)$$

Likewise, the stop delay measuring unit 109 calculates the X-ray exposure stop delay time Tb according to the following equation using the coordinate X4 calculated by equation (2) and the coordinate X5 at which the pixel value becomes constant after an increase:

$$Tb=(X5-X4)/Tf \quad (4)$$

As described above, this embodiment measures a delay associated with X-ray exposure by analyzing an image captured with uniform X-rays having constant intensity, in consideration of the fact that the charges stored in the detecting elements are read at a constant speed. That is, the embodiment measures delays based on the position of the boundary between a region where there is a change in pixel value and a region where there is no change in pixel value and the scanning speed associated with charge reading. The embodiment, in particular, measures, as the above delay, the time required to scan, at the scanning speed, the distance between the boundary and a detecting element of the flat panel detector which scans at the timing when the X-ray exposure signal (control signal) supplied from the control unit to the X-ray generator switches. According to the arrangement of the embodiment, therefore, it is possible to measure delay times associated with X-ray exposure easily at a low cost without scanning any special device other than the constituent elements of an existing X-ray imaging apparatus.

Although this embodiment has exemplified the case in which the following two delay times are measured, one of the following may be a target to be specified.

the delay from the instant an X-ray exposure signal switches from a signal indicating the stop of outputting of X-rays to a signal indicating outputting of X-rays to the instant the X-ray generator actually starts outputting X-rays (X-ray exposure start delay time); and the delay from the instant an X-ray exposure signal switches from a signal indicating outputting of X-rays to a signal indicating the stop of outputting of X-rays to the instant the X-ray generator actually stops outputting X-rays (X-ray exposure stop delay time).

Referring to FIG. 3, a pixel value read for each row is the value obtained by integrating X-ray intensities from time T3 when X-rays are actually emitted to the time when charges are read, and hence an X-ray intensity can be calculated by calculating a difference for each row. Displaying the calculated X-ray intensity, X-ray exposure signal, read signal, pixel value, and the like on the display unit 104 allows to visually check the timings of the signals as in a case in which they are measured by an oscilloscope.

The control unit 105 stores the measured X-ray exposure start delay time Ta and X-ray exposure stop delay time Tb in a storage device (not shown). It is possible to capture a good X-ray image by performing imaging by the technique disclosed in Japanese Patent Laid-Open No. 62-276798 using these measured values at the time of general imaging operation.

By using the above technique, the start delay measuring unit 108 can measure the X-ray exposure start delay time Ta, and the stop delay measuring unit 109 can measure the X-ray exposure stop delay time Tb.

This embodiment has exemplified the arrangement in which the delay time measuring unit 107 includes both the start delay measuring unit 108 and the stop delay measuring unit 109. The embodiment may be configured to include one of the start delay measuring unit 108 and the stop delay measuring unit 109.

This embodiment has exemplified the case in which the read sequence of the detecting elements coincides with the downward direction of the flat panel detector 103. However, the present invention is not limited to this. For example, it is possible to read charges from both sides of the flat panel detector 103, that is, downward and upward, or to read charges in a horizontal direction. In addition, the embodiment has exemplified the arrangement for driving the flat panel detector. However, the present invention is not limited to this. For example, it is possible to use a MIS photodiode.

In this embodiment, the pixel values shown in FIG. 3 are described as those on the vertical line 110 shown in FIG. 2. However, the present invention is not limited to this. For example, it is possible to use an average pixel value obtained by averaging pixel values for each row. Furthermore, the embodiment has exemplified the case in which the control unit 105 stores the measured X-ray exposure start delay time Ta and X-ray exposure stop delay time Tb. However, the present invention is not limited to this. For example, the X-ray generator 101 or the flat panel detector 103 may store them.

In addition, according to the above description, the timing control unit 106 sets an X-ray exposure signal Hi for about several ms. However, the present invention is not limited to this. For example, the timing control unit 106 may set the X-ray exposure signal Hi for the time input by an input device (not shown). Furthermore, the embodiment has exemplified the case in which the control unit 105 incorporates the timing control unit 106. However, the present invention is not limited to this. For example, the X-ray generator 101 or the flat panel detector 103 may incorporate the timing control unit 106.

The second embodiment of the present invention will be described next. An X-ray imaging apparatus according to this embodiment has an arrangement similar to that of the X-ray imaging apparatus of the first embodiment, in which a timing control unit 106 performs control to emit X-rays during charge reading as in the first embodiment. This embodiment differs from the first embodiment in that it emits X-rays a plurality of number of times, and performs a read for offset correction, a read during X-ray exposure, and a read for resetting detecting elements.

Figure 4:
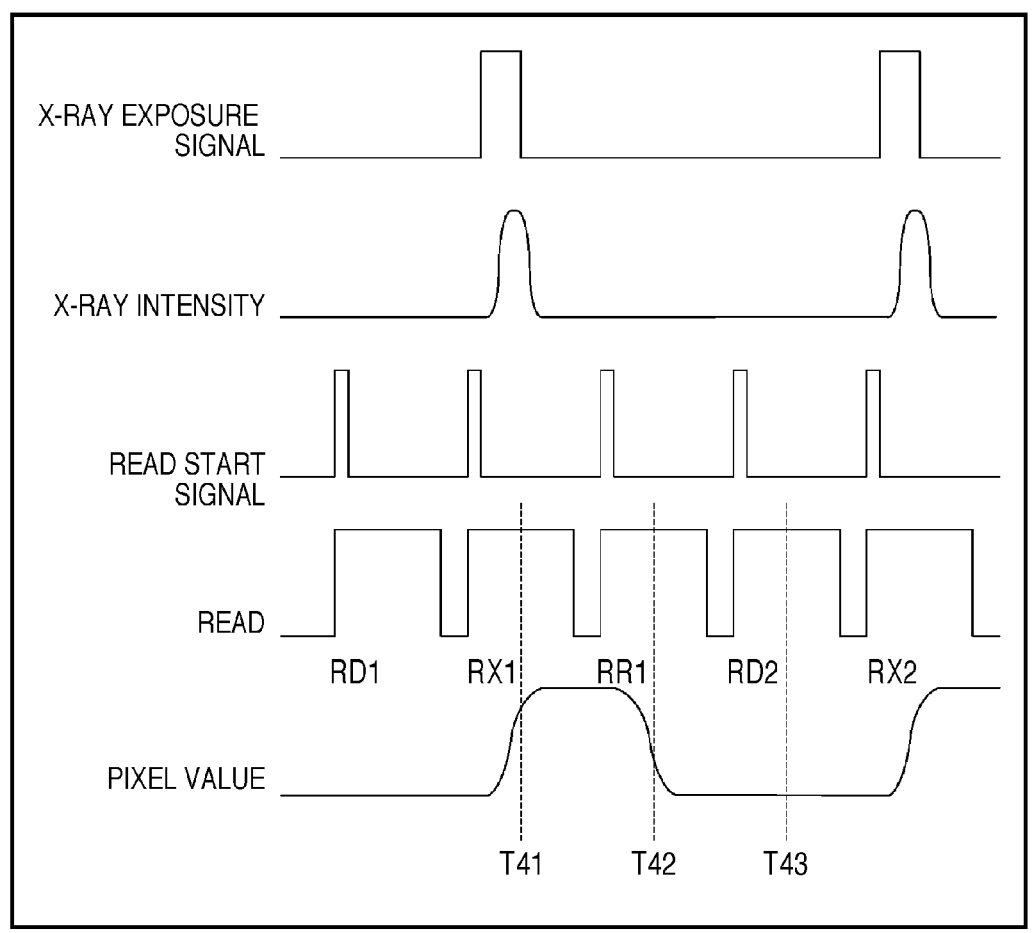

FIG. 4 is a timing chart showing an X-ray exposure signal, X-ray intensity, read start signal, read, and read pixel value in the moving image capturing mode. Referring to FIG. 4, reference symbol RD denotes a read without X-ray exposure; RX, a read with X-ray exposure; and RR, a read for resetting charges stored in detecting elements. Reference symbols RD1, RX1, and RR1 each denote the first read; and RD2 and RX2 each, the second read. A pixel value In (n is a natural number equal to or more than 1) of the nth offset-corrected image is obtained by equation (5). Note that RXn and RDn each indicate a pixel value read by the nth read.

$$In=RXn-RDn(n=1,2,\ldots) \quad (5)$$

A delay time measuring unit 107 including a start delay measuring unit 108 and a stop delay measuring unit 109 measures an X-ray exposure start delay time and an X-ray exposure stop delay time by analyzing the offset-corrected image In. A measurement procedure is the same as that in the first embodiment, and hence a description of it will be omitted.

In addition, the delay time measuring unit 107 performs X-ray exposure a plurality of number of times to measure an X-ray exposure start delay time and an X-ray exposure stop delay time a plurality of number of times. Of the X-ray exposure start delay times and X-ray exposure stop delay times measured a plurality of number of times, the maximum measured values are set as an X-ray exposure start delay time and an X-ray exposure stop delay time.

In addition, times T41 to T43 each are the time when charge is read from a coordinate X4 in FIG. 2, time T41 is the time during the read RX1, time T42 is the time during the read RD1, and time T43 is the time during the read RD2. The detecting element (the detecting element at the coordinate X4) from which charge is read at time T41 is reset after the charge is read. However, since X-ray exposure continues after time T41, the detecting element at the coordinate X4 detects X-rays again and stores charge. For this reason, when charge is read from the detecting element at the coordinate X4 at time T42, the pixel value obtained is the one obtained by X-ray exposure. When charge is read from the detecting element, the charge stored in the detecting element is reset thereafter. When, therefore, charge is read from the detecting element at the coordinate X4 at time T43, the obtained pixel value is the one obtained without X-ray exposure. For this reason, the image obtained by the read RD2 can be used as an offset-corrected image.

When performing offset correction a plurality of number of times in this manner, it is necessary to perform the read RD without X-ray exposure, the read RX with X-ray exposure, and the read RR for resetting the charge stored in the detector.

As described above, this embodiment measures delays associated with X-ray exposure operation by analyzing the difference image based on an image generated when X-rays are output and an image captured when no X-rays are output. Since the embodiment performs delay measurement by offset correction in this manner, it is possible to reduce measurement errors.

This embodiment performs offset correction by using equation (5). However, the present invention is not limited to this. For example, the read RD1 without X-ray exposure may be performed only once, and the second or subsequent reads RD2 without X-ray exposure may be omitted. In this case, the offset-corrected image In is calculated by $$In = RXn - RD1 (n=1, 2, \ldots) \quad (6)$$

This embodiment has exemplified the maximum values of measured values as an X-ray exposure start delay time and an X-ray exposure stop delay time. However, the present invention is not limited to this. For example, it is possible to use values obtained by adding times input via an input device (not shown) to the maximum X-ray exposure start delay time and X-ray exposure stop delay time.

The third embodiment of the present invention will be described next. An X-ray imaging apparatus according to this embodiment has an arrangement similar to that of the X-ray imaging apparatus according to the first embodiment, in which a timing control unit 106 performs control to emit X-rays during charge reading as in the first embodiment. This embodiment will exemplify a case in which an X-ray exposure time is long, and hence the time interval from the start of one X-ray exposure to the end of the X-ray exposure does not fall within a moving image read period.

Figure 5:
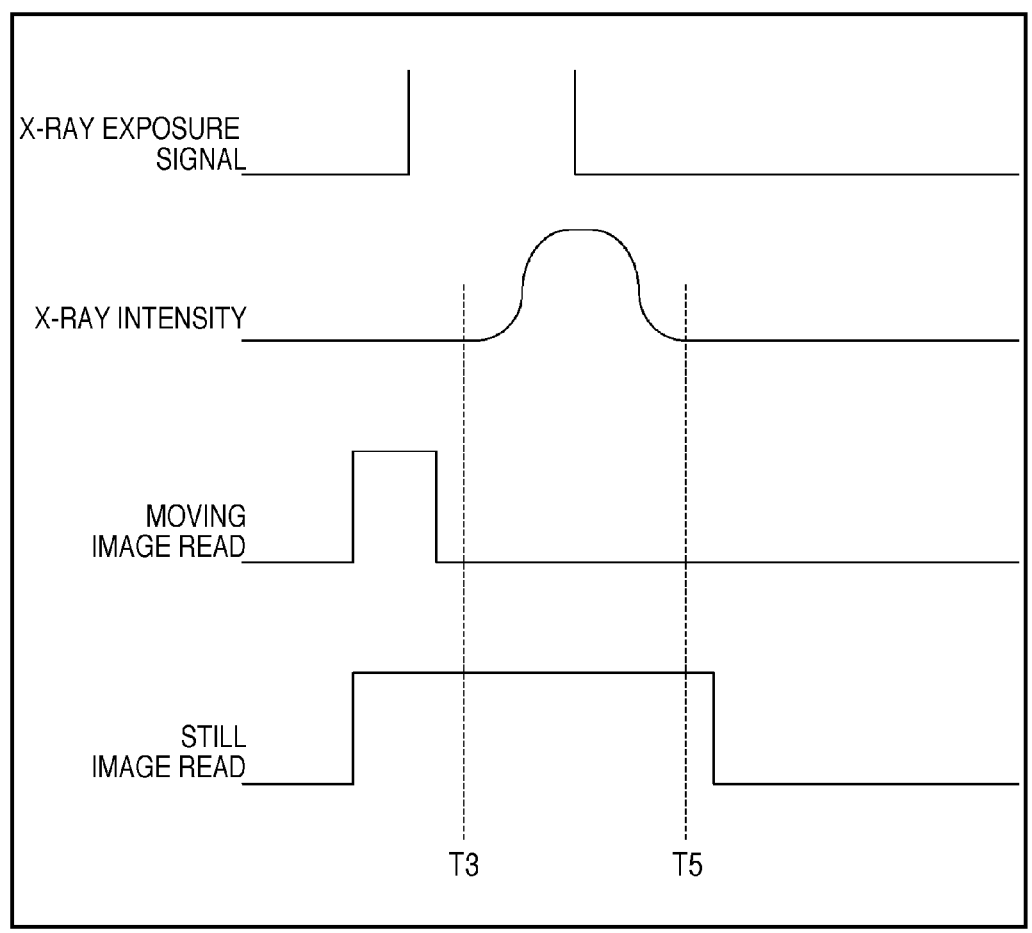

FIG. 5 is a timing chart showing an X-ray exposure signal, X-ray intensity, moving image read, still image read, and read pixel value in the moving image capturing mode. An illustration of "read start signal" will be omitted because it has already been described.

Referring to FIG. 5, time T3 is the time when X-ray exposure actually starts, and time T5 is the time when X-ray exposure actually stops. In the case shown in FIG. 5, the X-ray exposure start delay time and the X-ray exposure stop delay time are long, and hence times T3 and T5 do not fall within a moving image read period. In this case, a still image read with a long read period is performed to measure an X-ray exposure start delay time and an X-ray exposure stop delay time. Referring to FIG. 5, since a still image read period is long, times T3 and T5 fall within a still image read period. It is therefore possible to measure an X-ray exposure start delay time and an X-ray exposure stop delay time by using the above technique. Note, however, that since a still image read is performed in a time Tr different from a moving image read time Tf for each row, it is necessary to perform calculation according to equations (1) to (4) upon replacing Tf with Tr.

As described above, according to this embodiment, in the arrangement configured to read charges from the detecting elements at predetermined time intervals in a predetermined read period, when the time interval from the start of one X-ray exposure to the end of the X-ray exposure does not fall within a read period, the read period is prolonged (in the still image read period). This embodiment can therefore measure operation delays associated with X-ray exposure regardless of the environment in which the X-ray imaging apparatus performs moving image capturing.

This embodiment has exemplified a read in a long read time as a still image read. However, the present invention is not limited to this. Since a charge read time needs to be long, the time during which charges are read from one row of the flat panel detector may be set to a time other than the time Tr.

In addition, this embodiment has exemplified the case in which a moving image read is performed first, and a still image read is then performed. However, the present invention is not limited to this. For example, it is possible to perform a still image read in a long read time first.

The fourth embodiment of the present invention will be described next. An X-ray imaging apparatus according to this embodiment has an arrangement similar to that of the X-ray imaging apparatus according to the first embodiment, in which a timing control unit 106 performs control to emit X-rays during charge reading as in the first embodiment. The embodiment will exemplify a case in which an X-ray exposure time is long, and the time interval from the start of one X-ray exposure to the end of the X-ray exposure extends across a plurality of moving image read periods.

Figure 6:
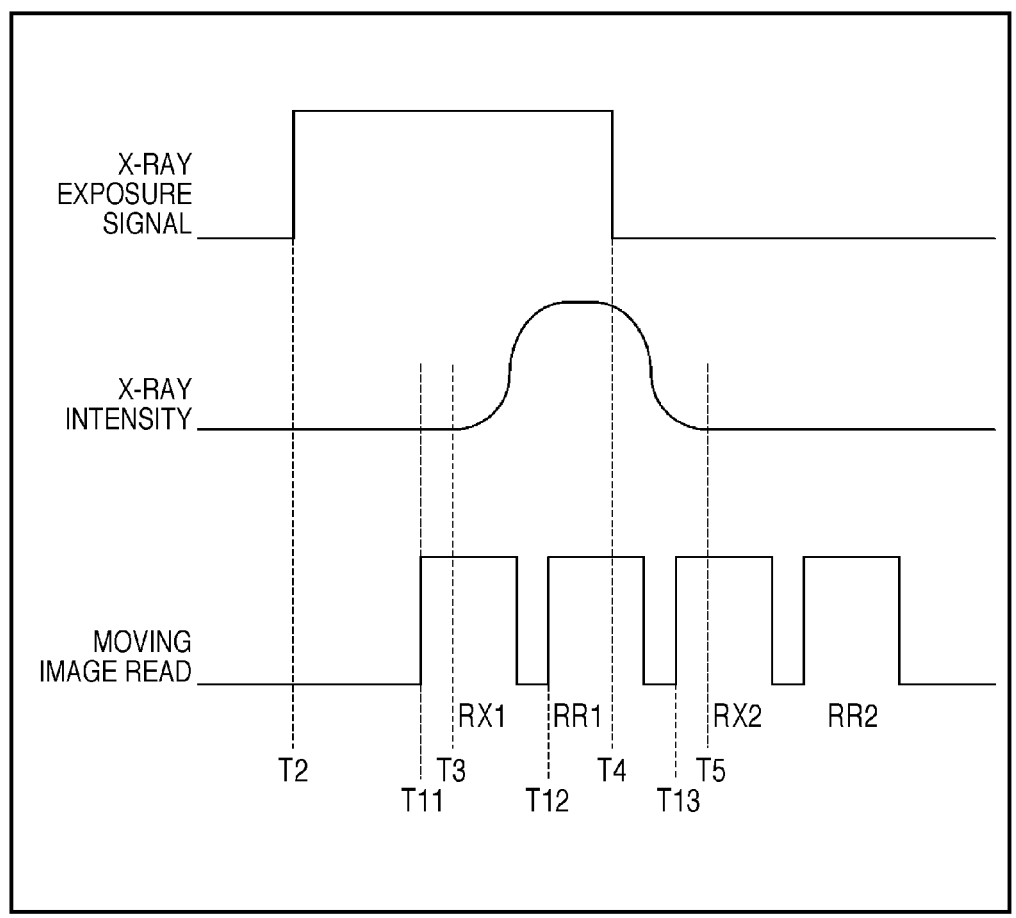

FIG. 6 is a timing chart showing an X-ray exposure signal, X-ray intensity, moving image read, and read pixel value at the time of moving image capturing. An illustration of "read start signal" will be omitted because it has already been described. An illustration of "read" without X-ray exposure for offset correction will be omitted because it has already been described in the second embodiment.

Referring to FIG. 6, reference symbol RX denotes a read with X-ray exposure; and RR, a read for resetting the charges stored in the detector. Reference symbols RX1 and RR1 each denote the first read; and RX2 and RR2 each, the second read. An illustration of "read RD" shown in FIG. 4 will be omitted because it has already been described. Time T11 is the time when the first read RX1 starts; time T12, the time when the first read RR1 starts; T13, the time when the second read RX2 starts; time T2, the time when an X-ray exposure signal is set Hi; time T3, the time when X-ray exposure actually starts;

time T4, the time when the X-ray exposure signal is set Lo; and time T5, the time when X-ray exposure actually stops.

Referring to FIG. 6, since the X-ray exposure start delay time and the X-ray exposure stop delay time are long, times T3 and T5 do not fall within one moving image read period. In this case, a moving image read is performed a plurality of number of times to measure X-ray exposure start delay times and X-ray exposure stop delay times. In addition, times T3 and T5 respectively fall within the first and second reads RX1 and RX2 upon adjustment of time T2 when the X-ray exposure signal is set Hi, time T11 when the first read RX1 starts, and time T4 when the X-ray exposure signal is set Lo.

A start delay measuring unit 108 calculates an X-ray exposure start delay time Ta according to equation (7) using a coordinate X3 at which the pixel value increases:

$$Ta = T11 - T2 + (X3 - X1)*Tf \qquad (7)$$

Likewise, the stop delay measuring unit 109 calculates an X-ray exposure stop delay time Tb according to equation (8) using a coordinate X5 at which the pixel value becomes constant after a coordinate X4 calculated by equation (2) described in the first embodiment is calculated, and the pixel value increases:

$$Tb = T13 - T12 - (X4 - X1)*Tf + (X5 - X1)*Tf \qquad (8)$$

As described above, this embodiment has exemplified the case in which the timing at which the X-ray exposure signal switches and the timing at which a detecting element existing at the boundary associated with the presence/absence of variation in pixel value in the captured image is operated for scanning respectively exist in different read periods. In such a case, as well as in the first embodiment, it is possible to measure operation delays associated with X-ray exposure.

Each arrangement described above can be applied to X-ray imaging apparatuses, more specifically X-ray imaging apparatuses as medical X-ray imaging apparatuses and industrial nondestructive examination apparatuses. As described above, the arrangement of each embodiment is configured to measure an X-ray exposure start delay time and an X-ray exposure stop delay time by performing X-ray exposure during a read and analyzing an X-ray image captured during X-ray exposure. This makes it possible to easily measure at least one of an X-ray exposure start delay time and an X-ray exposure stop delay time without increasing the cost.

The present invention can provide a technique of easily measuring delay times occurring at the start and stop of X-ray exposure at a low cost without providing any special arrangement.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-172728, filed on Jul. 30, 2010, which is hereby incorporated by reference herein in its entirety.

What is claimed is:

1. An X-ray imaging apparatus which obtains an X-ray image, the apparatus comprising:
    an imaging unit including a plurality of detecting elements adapted to convert X-rays generated by an X-ray generating apparatus which outputs or stops X-rays in accordance with an operation instruction into an image signal; and
    an obtaining unit adapted to obtain an operation start timing of the X-ray generating apparatus based on an image signal output from said imaging unit and obtain a difference between a timing of an operation instruction to the X-ray generating apparatus and the operation start timing.

2. The apparatus according to claim 1, further comprising a generating unit adapted to generate an image by sequentially operating the plurality of detecting elements for scanning at a constant speed and converting an image signal read from each detecting element into a pixel value,
    wherein said obtaining unit obtains, as the difference, a delay time of operation associated with outputting of X-rays from the X-ray generating apparatus relative to a timing of inputting of an operation signal to the X-ray generating apparatus by analyzing the generated image.

3. The apparatus according to claim 2, wherein said obtaining unit obtains the delay time based on a position of a boundary between a region where there is a change in pixel value in the image and a region where there is no change in pixel value and a speed of the scanning.

4. The apparatus according to claim 3, wherein said obtaining unit obtains, as the delay time, a time required to scan, at the speed of the scanning, a distance between the boundary and the detecting element operated to scan at a timing of inputting of the operation signal.

5. The apparatus according to claim 1, wherein said obtaining unit obtains a difference between the instant the operation instruction is issued and the instant the X-ray imaging apparatus actually starts outputting X-rays and a difference between the instant the operation instruction is issued and the instant the X-ray imaging apparatus actually stops outputting X-rays.

6. The apparatus according to claim 2, wherein said obtaining unit obtains the delay time by analyzing a difference image based on an image generated by said generating unit and an image captured when the X-rays are not output.

7. The apparatus according to claim 1, further comprising a reading unit adapted to sequentially operate the plurality of detecting elements for scanning at a constant speed and read image signals from the respective detecting elements,
    wherein said reading unit reads the image signal at predetermined time intervals in a predetermined read period, and
    reads the image signal upon prolonging the read period when a time interval from a start of one X-ray exposure to an end of the X-ray exposure does not fall within the read period.

8. The apparatus according to claim 1, further comprising a reading unit adapted to sequentially operate the plurality of detecting elements for scanning at a constant speed and read image signals from the respective detecting elements,
    wherein said reading unit reads the charge at predetermined time intervals in a predetermined read period, and reads the charge upon prolonging the read period when a time interval from a start of one X-ray exposure to an end of the X-ray exposure does not fall within the read period.

9. The apparatus according to claim 1, further comprising a control unit adapted to control a storage start timing of said imaging unit based on the obtained difference.

10. A method of measuring a delay time of X-ray exposure by an X-ray imaging apparatus which obtains an X-ray image, the method comprising the steps of:
   causing an X-ray generating apparatus to change an X-ray output state in accordance with an operation signal;
   sequentially reading image signals from an imaging unit adapted to convert the X-rays into image signals; and
   measuring a delay of operation of the generating apparatus relative to the operation signal by analyzing the image signal.

* * * * *